US011324392B2

(12) United States Patent
Parker (10) Patent No.: US 11,324,392 B2
(45) Date of Patent: May 10, 2022

(54) VACUUM STORAGE SYSTEM (71) Applicant: CANTEL (UK) LIMITED, Southend-on-Sea (GB)

(72) Inventor: George Christopher Parker, Westcliff-on-Sea (GB)

(73) Assignee: Cantel (UK) Limited, Southend-on-Sea (GB)

(*) Notice: Subject to any disclaimer, the term of this patent is extended or adjusted under 35 U.S.C. 154(b) by 0 days.

(21) Appl. No.: 16/293,131

(22) Filed: Mar. 5, 2019

(65) Prior Publication Data

US 2019/0191972 A1 Jun. 27, 2019

Related U.S. Application Data (63) Continuation-in-part of application No. 14/431,072, filed as application No. PCT/GB2013/052456 on Sep. 19, 2013, now abandoned.

(30) Foreign Application Priority Data

Sep. 26, 2012 (GB) ...................................... 1217216

(51) Int. Cl.
*A61B 1/00* (2006.01)
*A61B 50/33* (2016.01)
(Continued)

(52) U.S. Cl.
CPC .......... *A61B 1/00144* (2013.01); *A61B 50/30* (2016.02); *A61B 50/33* (2016.02); *B65B 31/04* (2013.01); *B65B 55/00* (2013.01); *B65D 51/1644* (2013.01); *B65D 53/02* (2013.01); *B65D 81/2015* (2013.01); *B65D 81/266* (2013.01); *A61B 2017/00734* (2013.01);
(Continued)

(58) Field of Classification Search
USPC .............................. 206/363, 364, 370, 524.8
See application file for complete search history.

(56) References Cited

U.S. PATENT DOCUMENTS 3,561,918 A * 2/1971 Ray ........................... A61L 2/20
422/119
3,943,987 A * 3/1976 Rossi ................. B65D 81/2015
206/524.8
(Continued)

FOREIGN PATENT DOCUMENTS

CN 102202595 A 9/2011
EP 1020371 7/2000
(Continued)

*Primary Examiner* — Jacob K Ackun
(74) *Attorney, Agent, or Firm* — Sorell, Lenna & Schmidt, LLP; William D. Schmidt, Esq.

(57) ABSTRACT

A vacuum storage system (40) for storing an article, comprises a sealable outer chamber (30) and a sealable inner chamber (20). The sealable outer chamber (30) has an evacuation valve (21) for connection to a suction device (48) for evacuation of said outer chamber (30). The sealable inner chamber (20) is adapted to receive said article and has a one-way valve (13) in communication with the outer chamber (30). The one-way valve (13) is adapted to open upon the application of suction to the outer chamber (30), thereby to enable evacuation of said inner chamber (20), but to close upon discontinuation of said suction.

10 Claims, 9 Drawing Sheets

(51) Int. Cl.
  B65B 31/04 (2006.01)
  B65B 55/00 (2006.01)
  B65D 53/02 (2006.01)
  B65D 81/20 (2006.01)
  B65D 81/26 (2006.01)
  B65D 51/16 (2006.01)
  A61B 50/30 (2016.01)
  A61B 50/00 (2016.01)
  A61B 17/00 (2006.01)

(52) U.S. Cl.
  CPC . *A61B 2050/005* (2016.02); *A61B 2050/0066* (2016.02); *A61B 2050/3015* (2016.02); *A61B 2050/314* (2016.02)

(56) References Cited

U.S. PATENT DOCUMENTS

| | | | |
|---|---|---|---|
| 4,909,014 A | 3/1990 | Kobayashi | |
| 5,310,524 A | 5/1994 | Campbell | |
| 5,378,428 A | 1/1995 | Inoue et al. | |
| 5,526,928 A * | 6/1996 | Yabe | A61B 1/121 206/363 |
| 5,534,221 A | 7/1996 | Hillebrenner et al. | |
| 6,164,738 A | 12/2000 | Dane et al. | |
| 6,312,645 B1 | 11/2001 | Lin et al. | |
| 6,749,063 B2 | 6/2004 | Parker | |
| 8,100,263 B2 * | 1/2012 | Vanderbush | B65B 5/067 206/524.8 |
| 8,434,633 B2 * | 5/2013 | Beer | B65D 77/225 220/89.1 |
| 8,747,739 B2 | 6/2014 | Parker et al. | |
| 2003/0015452 A1 * | 1/2003 | Su | B65D 81/2038 206/524.8 |
| 2003/0138347 A1 | 7/2003 | Lin | |
| 2004/0188304 A1 | 9/2004 | Bonnette et al. | |
| 2005/0035021 A1 * | 2/2005 | Higer | B65D 81/2015 206/524.8 |
| 2005/0147527 A1 | 7/2005 | Brown et al. | |
| 2005/0268573 A1 | 12/2005 | Yan | |
| 2007/0007163 A1 * | 1/2007 | Schlattl | B65D 81/2038 206/543 |
| 2007/0215510 A1 * | 9/2007 | Sung | B65D 79/005 206/524.8 |
| 2008/0190512 A1 * | 8/2008 | Borchardt | B65D 81/2038 141/8 |
| 2008/0230429 A1 * | 9/2008 | Anderson | B65D 81/2038 206/524.8 |
| 2008/0304771 A1 * | 12/2008 | Harder | B65D 33/25 383/63 |
| 2009/0050512 A1 * | 2/2009 | Pham | B65D 77/225 206/524.8 |
| 2009/0123333 A1 * | 5/2009 | Parker | A61B 50/00 422/33 |
| 2009/0232423 A1 * | 9/2009 | Sabounjian | B65D 33/2541 383/100 |
| 2011/0192744 A1 | 8/2011 | Parker | |
| 2013/0105344 A1 * | 5/2013 | Hartley | A61B 50/36 206/363 |
| 2014/0353203 A1 * | 12/2014 | Hu | B65D 77/225 206/524.8 |
| 2015/0122681 A1 * | 5/2015 | Dacey | A61B 50/30 206/363 |

FOREIGN PATENT DOCUMENTS

| | | |
|---|---|---|
| EP | 1020371 A2 | 7/2000 |
| GB | 2226015 | 6/1990 |
| GB | 2226015 A | 6/1990 |
| GB | 2381521 | 5/2003 |
| JP | 1987054967 | 4/1987 |
| JP | H10-228864 | 9/1998 |
| JP | 2005126091 | 5/2005 |
| JP | 2009513213 | 2/2009 |
| WO | 2005073091 | 8/2005 |
| WO | 2005120395 | 12/2005 |
| WO | 2007049076 | 5/2007 |
| WO | 2007049076 A1 | 5/2007 |
| WO | 2012091521 | 7/2012 |
| WO | 2012091521 A2 | 7/2012 |

* cited by examiner

VACUUM STORAGE SYSTEM

CROSS REFERENCE TO RELATED APPLICATION

This application is a continuation in part of U.S. application Ser. No. 14/431,072, filed on Sep. 19, 2013, the entire contents of which is incorporated herein by reference.

BACKGROUND

This application relates to a method and apparatus for storing an article. In particular, the application relates to a method and apparatus for storing an article of medical equipment, such as a flexible medical endoscope, in a state of high level disinfection following processing (cleaning and disinfection) thereof. However, it is envisaged that the method and apparatus of the present application may find use in the storage of a wide range of articles, such as museum artefacts, botanical samples, or indeed any other articles for which storage in a reduced oxygen atmosphere would be beneficial.

The term "disinfection" is used herein in preference to the term "sterility" since the latter implies the complete absence of pathogenic organisms, which in practice is rarely, if ever, achievable. It is to be appreciated however that the ultimate aim of disinfecting medical equipment is indeed to get as close to absolute sterility as is practicable. The terms "vacuum", "evacuation", "evacuate" and "evacuated" as used herein should be understood in their everyday sense to mean a partial vacuum such as can readily be achieved with standard commercial or laboratory equipment.

The present application has been developed particularly for use in connection with the storage of flexible medical endoscopes in a state of high level disinfection following processing (cleaning and disinfection), and therefore will be described herein with particular emphasis on this application. It is envisaged however, that the method of the present application may be utilised for the storage of substantially all types of medical, surgical, dental and veterinary equipment, apparatus, and instruments, and indeed in other applications outside the medical field, such as museum artefacts, botanical samples, or any other articles where storage in an evacuated container or a reduced oxygen atmosphere may be desirable.

After use in an endoscopic procedure, flexible medical endoscopes are usually subjected to "processing", consisting of rigorous manual cleaning followed by placing the endoscope in an Automated Endoscope Re-processor (AER) which effects a further cleaning and disinfecting procedure to bring the endoscope to High Level Disinfection Status (HLDS). The endoscope must then be stored in a clean environment. Under normal storage conditions, the degree of disinfection of the endoscope can only be maintained at an acceptable level for a relatively short period, usually about 3 hours. This is due to the multiplication of residual pathogens which may remain on the endoscope after disinfection, or which may be present in the atmosphere. If the endoscope is not used in a further endoscopic procedure within this time, then further processing will be necessary prior to its next use.

Frequent and repeated processing is undesirable, since it reduces the availability of the endoscope for endoscopic procedures, whilst increasing the operating costs, due to the need for cleaning and disinfectant materials and the operation of cleaning equipment. Furthermore, repeated processing reduces the lifetime of the endoscope due to wear and tear.

In view of the above, attempts have been made to prolong the length of time for which a processed endoscope can be stored in a viable HLDS condition. One approach which has proved successful to some degree is to store the endoscope in an evacuated chamber, such as a vacuum storage pouch or bag. This deprives aerobic micro-organisms within the chamber of the oxygen they require in order to multiply, though since total evacuation of the chamber cannot practically be achieved, it is not possible totally to prevent the growth of aerobic micro-organisms. Nevertheless, the length of time for which a processed endoscope can be stored in a viable HLDS condition can be appreciably extended by such methods. Methods and apparatus involving the prolonged storage of an endoscope in an evacuated chamber are disclosed in the Applicant's own International Patent Publications Nos. WO 2007/049076, WO 2010/046617 and WO 2012/035313.

In a clinical environment, the quality of the partial vacuum achieved will generally be restricted to a low to medium vacuum (100 kPa to 1 kPa) by the limitations of the standard commercial or laboratory evacuation equipment utilised, as well as the physical properties of the evacuation chamber. In view of these constraints, the integrity of the seal by which the evacuation chamber is closed becomes a major factor in determining the extent to which the viable storage time of an endoscope can be prolonged. This is of particular concern when utilising standard vacuum storage bags of flexible pouch construction, as the zip seals on such bags tend to fail or leak after a period of time, thus compromising the high level disinfection status of the endoscope.

Therefore, it would be beneficial to provide a vacuum storage system comprising a tray that engages a rigid lid comprising a one-way valve, and a flexible pouch comprising an evacuation valve such that when the tray and lid are inserted into the pouch and the pouch is sealed, suction from a vacuum can be applied to the system such that a tight seal can be created between the tray and the lid. It would also be beneficial to provide the rigid tray with the one-way valve so that upon application of suction from the vacuum, the one-way valve would open, causing a passageway into an inner compartment of the tray to remove air within the inner compartment and when suction is discontinued, the one-way valve closes, thereby maintaining a closed environment for the processed endoscope.

SUMMARY

A vacuum storage system is provided that incorporates a fail-safe arrangement comprising a flexible vacuum pouch, a one-way valve disposed on a rigid lid, and a tray, where the lid engages and seals with the tray when suction is applied such that the vacuum within a storage chamber is maintained even if the integrity of the seal is compromised.

According to a first aspect of the present disclosure there is provided a vacuum storage system for storing an article, comprising:

a sealable outer chamber, having an evacuation valve for connection to a suction device for evacuation of said outer chamber; and a sealable inner chamber adapted to receive said article, and having a one-way valve in communication with the outer chamber, said one-way valve being adapted to open upon the application of suction to the outer chamber, thereby to enable evacuation of said inner chamber, but to close upon discontinuation of said suction.

The article to be stored may be an article of medical equipment, such as a flexible medical endoscope.

The inner chamber may itself be a flexible pouch or bag. However, in some embodiments, the inner chamber comprises a tray and a lid of generally rigid construction. In some embodiments, the one-way valve is formed in the lid.

A gasket seal is preferably provided between the tray and the lid. The gasket seal is preferably housed in the lid and arranged to extend around the perimeter of the tray, when the lid and tray are engaged. Upon evacuation of the system, the lid is urged onto the tray, thus compressing the gasket seal to seal the inner chamber.

The interior of the tray may be desirably be shaped or sculpted so as securely to house the article to be stored. This may be take the form of upstanding elements arranged to embrace and protect an article, or parts of an article, such as the coils of a flexible medical endoscope.

The outer chamber preferably comprises a flexible pouch or bag, having an opening to enable insertion of the inner chamber. The opening is preferably provided with a zip seal and/or an adhesive seal. An evacuation valve, adapted for connection to a suction device, is provided in one wall of the pouch. The evacuation valve may itself be a one-way valve.

In use, evacuation of the outer chamber pouch causes the one-way valve in the tray lid to open, thus enabling evacuation of the inner chamber. Evacuation of the outer chamber pouch also causes the pouch to urge the lid onto the tray, thus causing compression of the gasket seal, and so sealing the inner chamber.

The inner and outer chamber are preferably both transparent, to enable the contents of the vacuum storage system to be conveniently viewed.

In order further to enhance the efficiency of the storage system according to the first aspect of the present disclosure, an oxygen scavenging agent may optionally be provided within the inner chamber, as further to reduce the oxygen content of the atmosphere in which the article is stored.

According to a second aspect of the present disclosure there is provided a method of storing an article utilizing a vacuum storage system as hereinbefore described, comprising the steps of: inserting the article to be stored into the inner chamber of said vacuum storage system; sealing the inner chamber; inserting the inner chamber into the outer chamber of said vacuum storage system; sealing the outer chamber; connecting the evacuation valve of the outer chamber to a suction device; activating the suction device so as to evacuate the outer chamber, thereby to cause the one-way valve of the inner chamber to open, so as also to evacuate the inner chamber; deactivating the suction device so as to close the one-way valve, thus isolating the article in the evacuated inner chamber; and closing the evacuation valve, thus isolating the inner chamber in the evacuated outer chamber.

In order further to enhance the efficiency of the storage method according to the second aspect of the present disclosure, the method may optionally include an additional step of providing an oxygen scavenging agent within the inner chamber, as further to reduce the oxygen content of the atmosphere in which the article is stored.

BRIEF DESCRIPTION OF THE DRAWINGS

In order that the present disclosure may be more clearly understood, embodiments thereof will now be described in detail, though only by way of example, with reference to the accompanying drawings in which:

FIG. 13 shows a perspective view of the tray of FIG. 1 disposed inside of the flexible pouch of FIG. 4. When a suction device, such as a vacuum is attached to an evacuation valve of the pouch, suction from the vacuum urges the lid of FIG. 2 onto the tray to form a sealable inner chamber. A one-way valve of either of FIGS. 11A-11E disposed on the lid opens upon application of suction from the vacuum such that air within an inner chamber of the tray is evacuated from the inner chamber. After application of suction, the one-way valve closes and the pouch shrinks entirely around the tray, which also assists in urging the lid of FIG. 2 onto the tray to form a sealable inner chamber.

DETAILED DESCRIPTION

Figure 1:
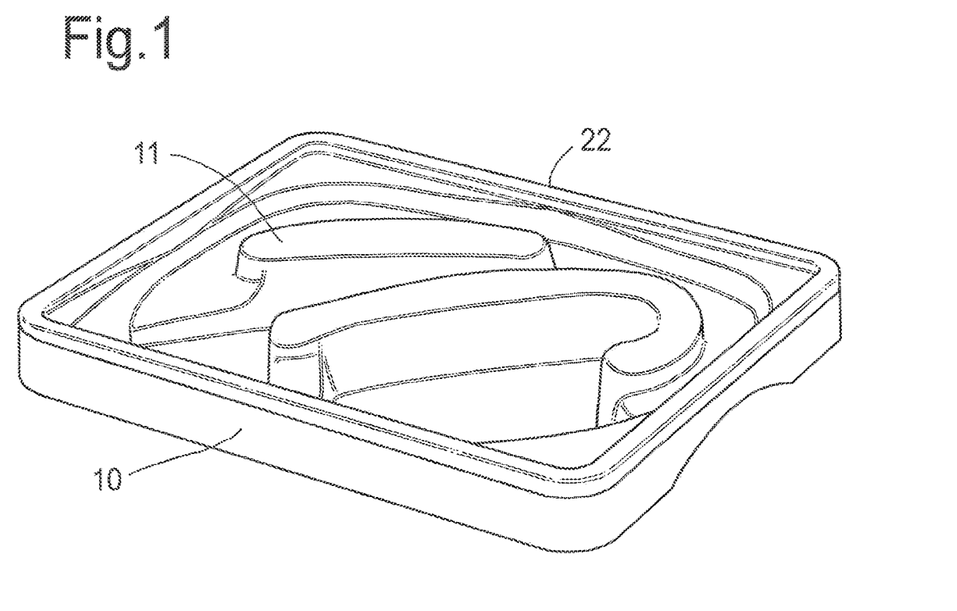
FIG. 1 shows a tray, constituting a first part of an inner chamber of an embodiment of vacuum storage system according to the present disclosure.
Figure 9:
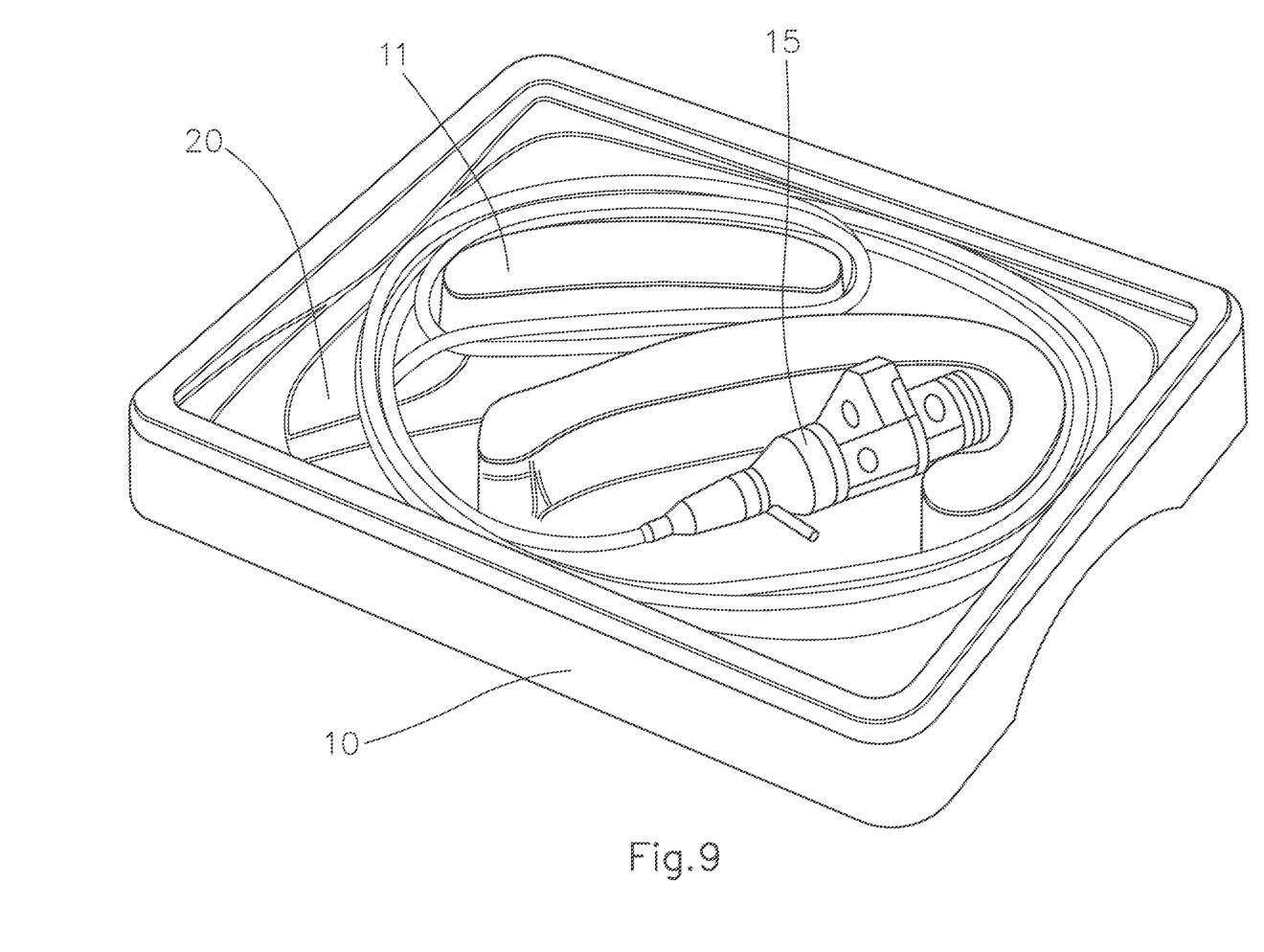
FIG. 9 shows a perspective view of the tray of FIG. 1 and an endoscope that is stored in the inner chamber of the tray and the upstanding elements contouring and supporting a flexible medical endoscope in a stress-free state.
Figure 10:
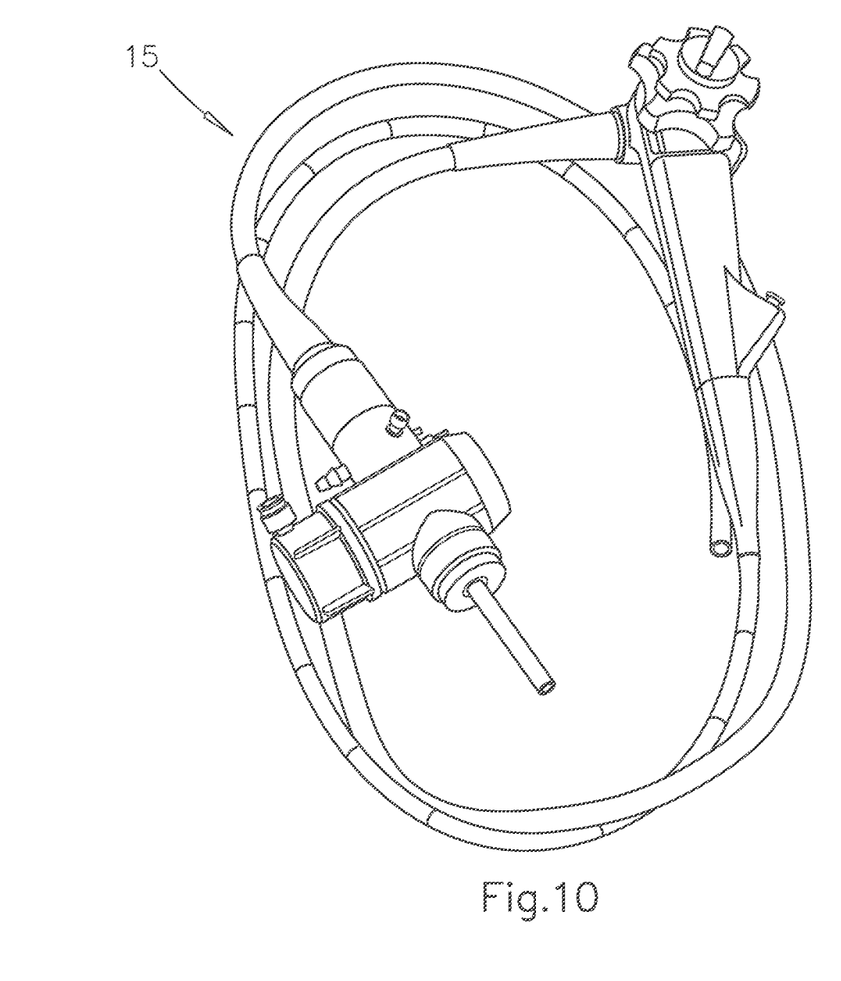
FIG. 10 shows a perspective view of the endoscope of FIG. 9.

Referring first to FIG. 1, there is shown a tray 10 of generally rigid construction, constituting a first part of an inner chamber of an embodiment of the vacuum storage system according to a first aspect of the present disclosure. The tray 10 is shaped and sculpted with upstanding elements 11 arranged to embrace and protect the coils of a flexible medical endoscope 15 when stored therein, as shown in FIGS. 9 and 10. In some embodiments, the upstanding elements 11 contour the components of the endoscope 15 when the endoscope is stored within the tray 10. In some embodiments, endoscope 15 can be an Olympus®, Pentax®, or FujiFilm® endoscope.

In some embodiments, dimensions of tray 10 are sufficient to accommodate therein substantially all sizes of endoscopes 15 in a coiled state without undue stress being applied to the flexible portions of endoscope 15. In some embodiments, tray 10 is configured to store endoscope 15 in a stress free state. In some embodiments, tray 10 can be sized to permit it to be easily carried by a person.

Figure 2:
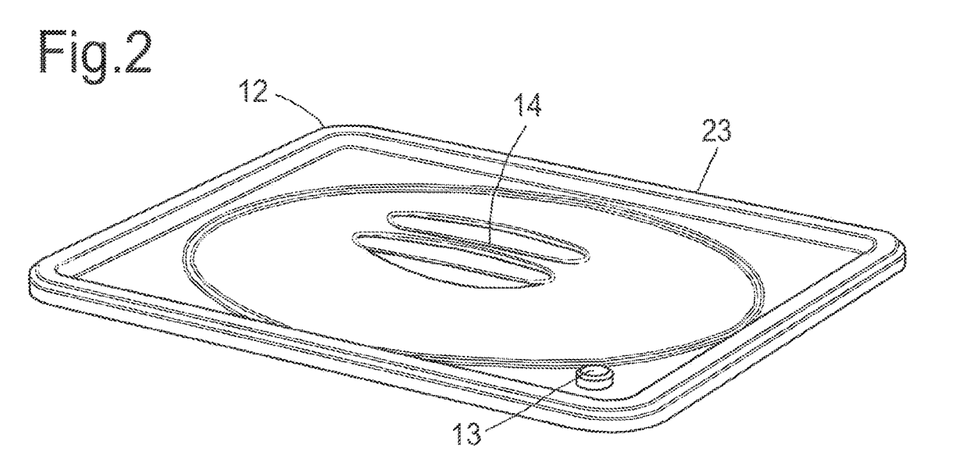
FIG. 2 shows a lid, constituting a second part of the inner chamber.

Referring now to FIG. 2, there is shown a lid 12, constituting a second part of the inner chamber of the vacuum storage system according to the present disclosure. The lid 12 is also of generally rigid construction and is of complementary size and shape to the tray 10, and adapted to engage therewith. The lid 12 has a one-way valve 13 formed therein to enable evacuation of the inner chamber, as will be described in more detail below. The lid 12 is transparent, to enable the contents of the inner chamber to be viewed, and has finger grips 14 to facilitate removal of the lid 12 from the tray 10 after use.

Figure 3:
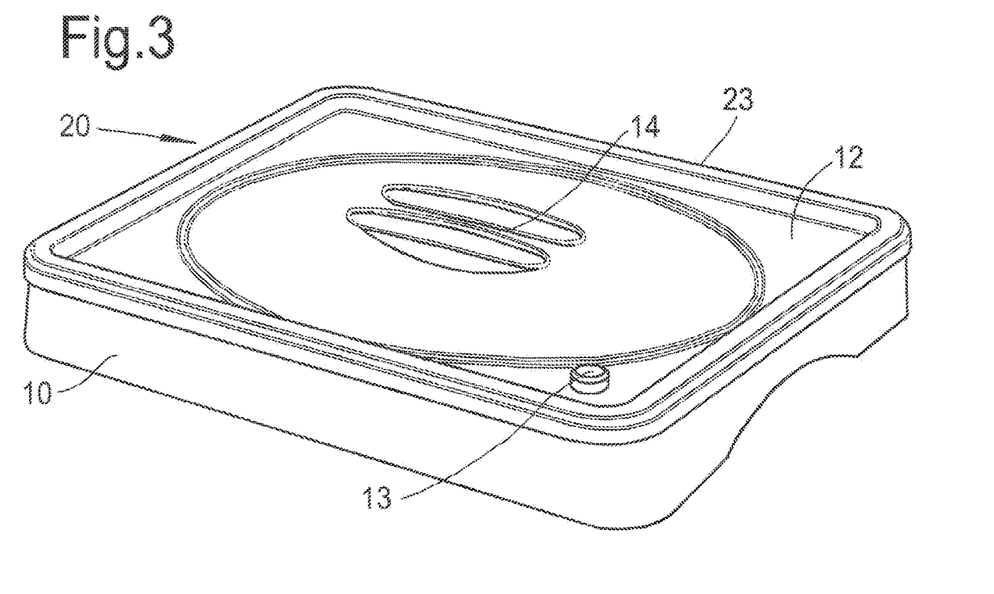
FIG. 3 shows the tray of FIG. 1 combined with the lid of FIG. 2 to form the inner chamber.

Referring now to FIG. 3, this shows the lid 12 engaged with the tray 10 in order to form a sealable inner chamber, generally indicated 20, of a vacuum storage system according to the present disclosure. The one-way valve 13 now communicates with the air-space within the inner chamber 20, as defined by the lid 12 and tray 10.

The one-way valve 13 includes a valve that allows fluid (liquid or gas) to flow through it in only one direction thereby preventing any backward flow. Conventional one-way valves can be used that are provided in the lid that allow fluid (liquid or gas) to flow through it in only one direction thereby preventing any backward flow. The one-way valve 13 can be controlled by the pressure applied to the valve and will open when the pressure inside and the pressure outside of the valve are different. In some embodiments, an evacuation valve 21 described below can also be a one-way valve. Therefore, in some embodiments, both the valve of the lid and the evacuation valve can be one-way valves.

In some embodiments, the tray 10 engaged with lid 12 are configured to be disposed within a flexible pouch 16, as described below. When suction is applied to the pouch 16, at evacuation valve 21, which can also be a one-way valve, the one-way valve 13 of the lid is configured to open and release air flowing from inner chamber 20 and out into an outer chamber 30 of flexible pouch 16. In some embodiments, the one-way valve 13 is configured to fluidly couple the inner chamber 20 to outer chamber 30 of pouch 16.

Figure 11A:
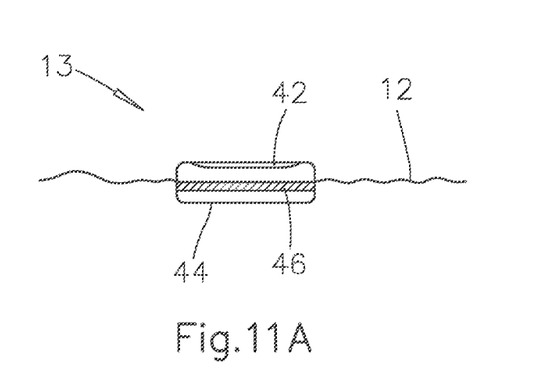
FIG. 11A shows a side view of an embodiment of a one-way valve of the lid of FIG. 2.

The one-way valve 13 comprises an outlet 42 configured to release air flowing from the inner chamber 20 of the tray 10, an inlet 44 to allow air from the inner chamber 20 to enter the one-way valve 13 when suction is applied, and a seal 46 that allows only air to enter the inlet 44 for release out of the outlet 42, as shown in FIG. 11A. The seal 46 is disposed between the inlet 44 and the outlet 42 and is a movable barrier configured to reduce or prevent contaminants from entering into the inner chamber 20 of the tray 10.

Figure 11B:
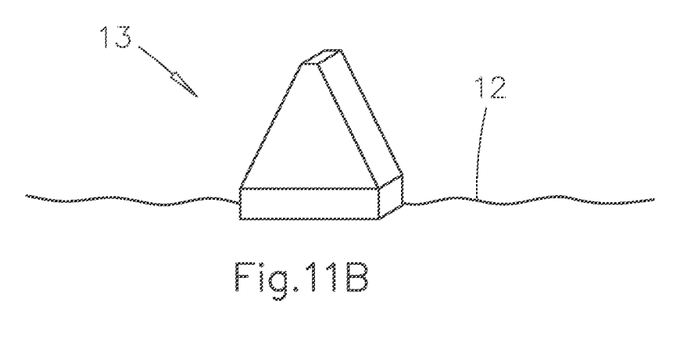
FIG. 11B shows a side view of an embodiment of a one-way valve of the lid of FIG. 2, where the one-way valve is a duckbill valve.
Figures 11C, 11D:
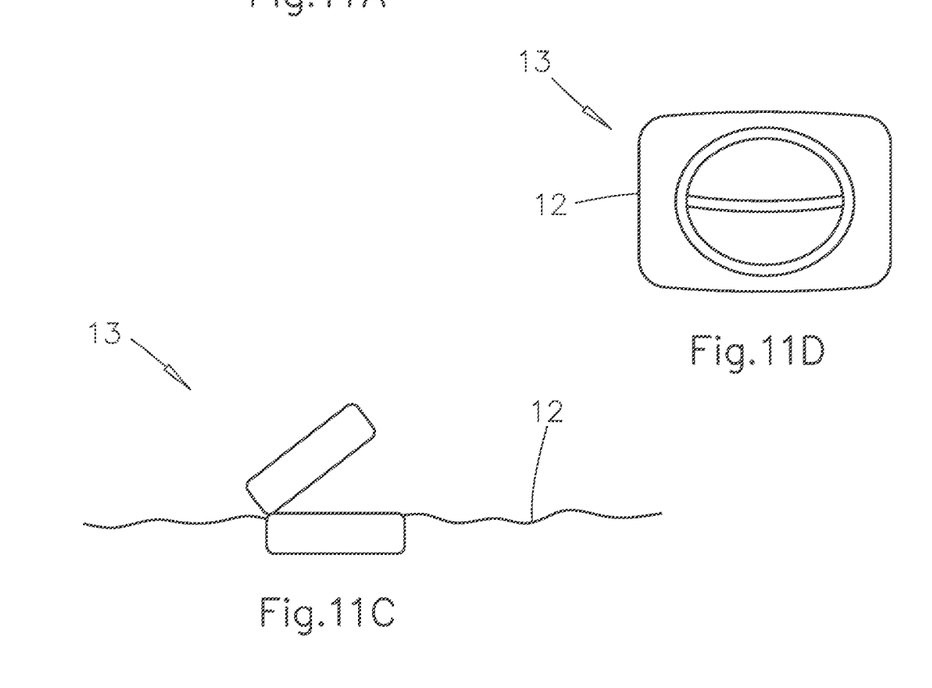
FIG. 11C shows a side view of an embodiment of a one-way valve of the lid of FIG. 2, where the one-way valve is a flap valve.
FIG. 11D shows a top view of an embodiment of a one-way valve of the lid of FIG. 2, where the one-way valve includes a slit.
Figure 11E:
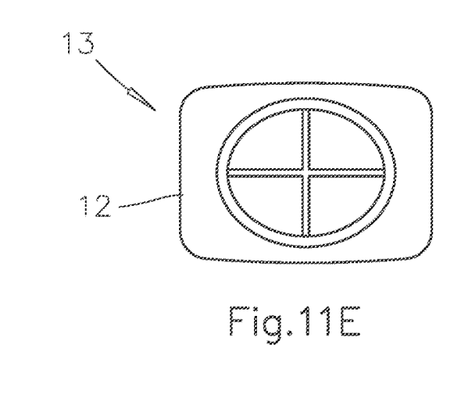
FIG. 11E shows a top view of an embodiment of a one-way valve of the lid of FIG. 2, where the one-way valve includes two slits in a cross shaped configuration.

In some embodiments, the one-way valve 13 can be a pressure valve or a degassing valve, as shown in FIG. 11A, a duckbill valve, as shown in FIG. 11B, a flap valve, as shown in FIG. 11C, a valve comprising a single slit diaphragm, as shown in FIG. 11D or a valve comprising a double or cross shaped slit diaphragm, as shown in FIG. 11E.

Figure 13:
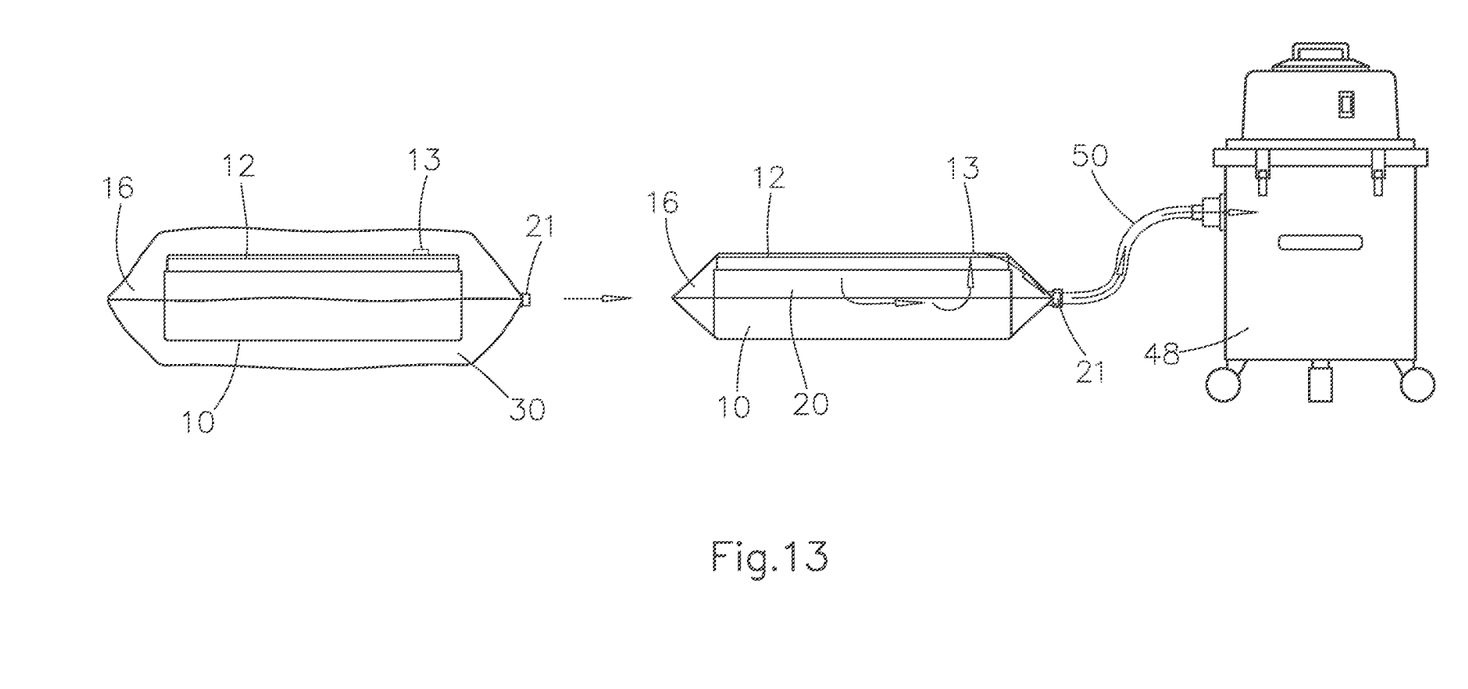

The one-way valve 13 is a controlling device for the passage of suction in one direction and is controlled by the suction applied to the one-way valve 13 by a suction device 48, such as a vacuum, as shown in FIG. 13. For example, the one-way valve 13 will be closed when no suction is provided, however, when suction is provided, the suction will force the one-way valve 13 to open, thereby releasing air from inner chamber 20 and out into outer chamber 30. It is to be understood that the one-way valve 13 is a valve that allows the passage of air in one direction and that the one-way valve 13 will open when the pressure or suction outside of the inner chamber 20 is less than the pressure inside the inner chamber 20. The one-way valve 13 will close when pressure difference between the outer chamber 30 and the inner chamber 20 is not significantly different.

The one-way valve 13 can be positioned within or on the lid 12 in a few ways. For example, the one-way valve 13 can be centrally attached to the lid 12 adjacent to finger grips 14 or can be attached to one of the edges of the lid 12. In some embodiments, the one-way valve 13 is monolithically formed with the lid 12 or is attached to the lid 12 by an adhesive, a friction fitting and/or tape.

In some embodiments, the one-way valve 13 can be made from a material, such as, for example, polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), rubber, plastic (e.g., polycarbonates), ABS, MABS, silicone, or the like or combinations thereof.

Figure 4:
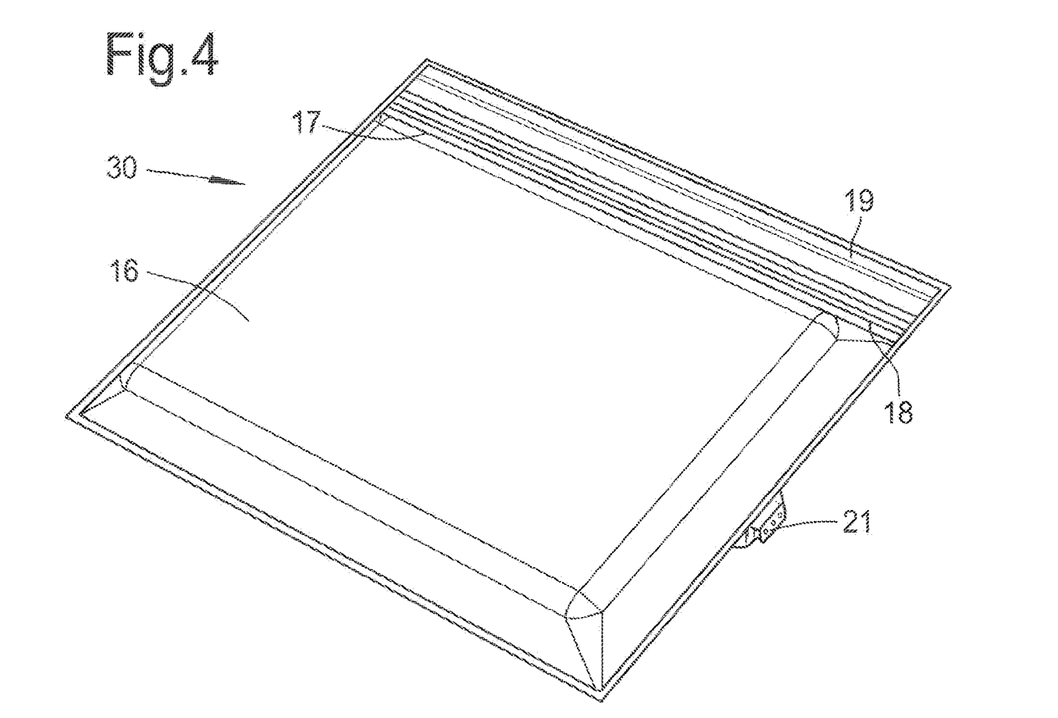
FIG. 4 shows a flexible pouch, constituting an outer chamber of the vacuum storage system.

Referring now to FIG. 4, there is shown flexible pouch 16, as described above, constituting the sealable outer chamber 30 of the vacuum storage system according to the present disclosure. In some embodiments, the pouch 16 is collapsible and/or deformable. As with the lid 12, the pouch 16 is transparent to enable the contents to be viewed. The pouch 16 has an opening 17, to enable insertion of the inner chamber 20, provided with a double zip seal 18 and/or an adhesive seal 19. The evacuation valve 21 is adapted for connection to suction device 48 (FIG. 13) for evacuation of the pouch 16, and is provided in one wall thereof. The evacuation valve 21 can also be a one-way valve. Conventional one-way valves can be used as the evacuation valve 21 that allows fluid (liquid or gas) to flow through it in only one direction thereby preventing any backward flow. The evacuation valve 21 can be controlled by the pressure applied to the valve and will open when the pressure inside and the pressure outside of the valve are different. For example, when the pressure is greater inside the valve than outside the valve, the valve will open. When the pressure outside the valve is greater than the pressure inside the valve, the valve will close.

Figures 12A, 12B, 12C, 12D, 12E:
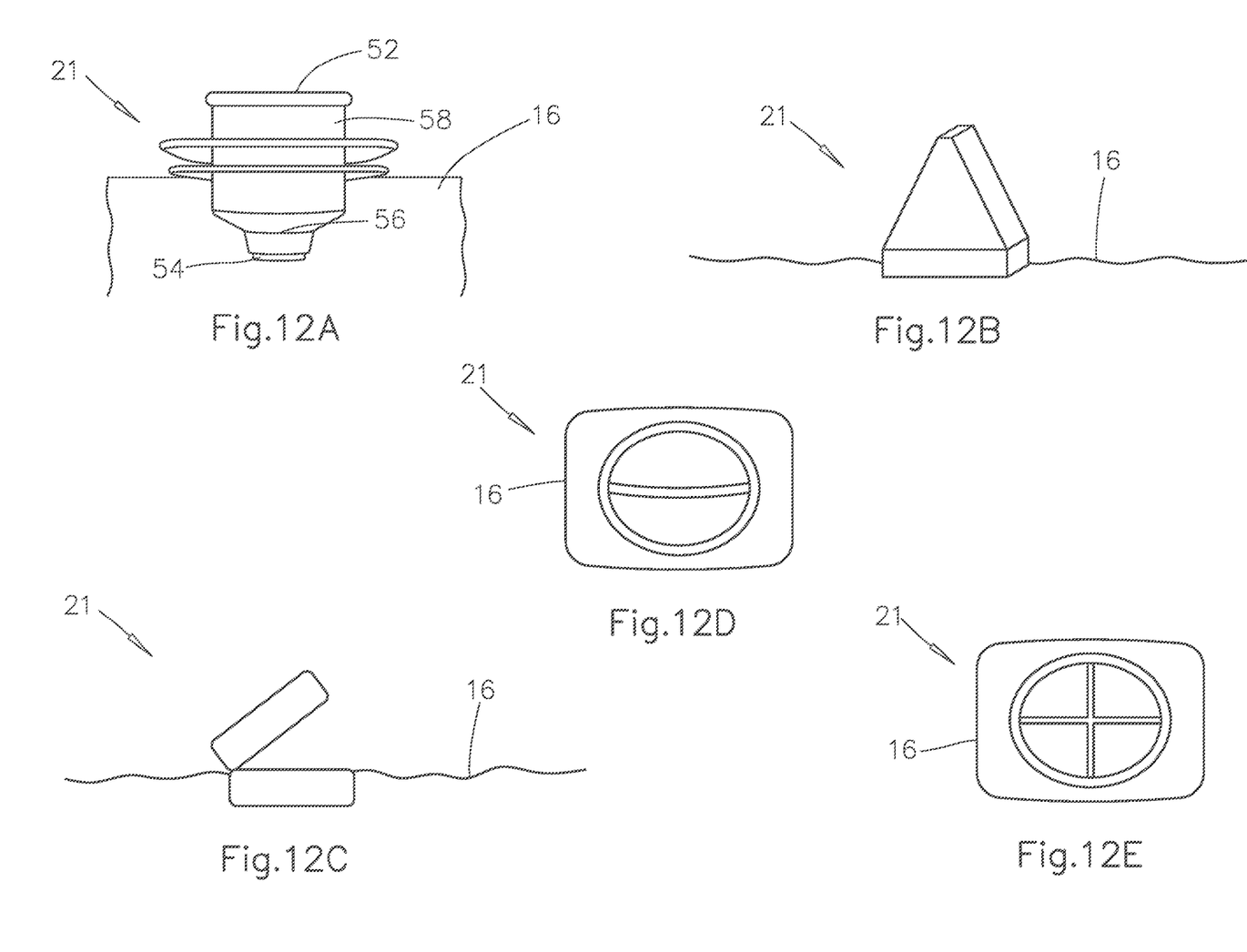
FIG. 12A shows a side view of an embodiment of an evacuation valve of the flexible pouch of FIG. 4, where the evacuation valve is a one-way valve.
FIG. 12B shows a side view of an embodiment of an evacuation valve of the flexible pouch of FIG. 4, where the evacuation valve is a duckbill valve.
FIG. 12C shows a side view of an embodiment of an evacuation valve of the flexible pouch of FIG. 4, where the evacuation valve is a flap valve.
FIG. 12D shows a top view of an embodiment of an evacuation valve of the flexible pouch of FIG. 4, where the evacuation valve includes a slit.
FIG. 12E shows a top view of an embodiment of an evacuation valve of the flexible pouch of FIG. 4, where the evacuation valve includes two slits in a cross shaped configuration.

The evacuation valve 21 comprises an outlet 52, as shown in FIG. 12A, configured to release air flowing from the outer chamber 30 of pouch 16 and the inner chamber 20 of the tray 10 when a vacuum hose 50 of suction device 48 is attached to an engagement surface 58 of the evacuation valve 21 and suction is applied. The evacuation valve 21 includes an inlet 54 to allow air from the outer chamber 30 and the inner chamber 20 to enter the evacuation valve 21 when suction is applied, and a seal 56 that allows only air to enter the inlet 54 for release out of the outlet 52, as shown in FIG. 12A. The seal 56 is disposed between the inlet 54 and the outlet 52 and is a movable barrier configured to reduce or prevent contaminants from entering into the outer chamber 30 and the inner chamber 20.

Figure 8:
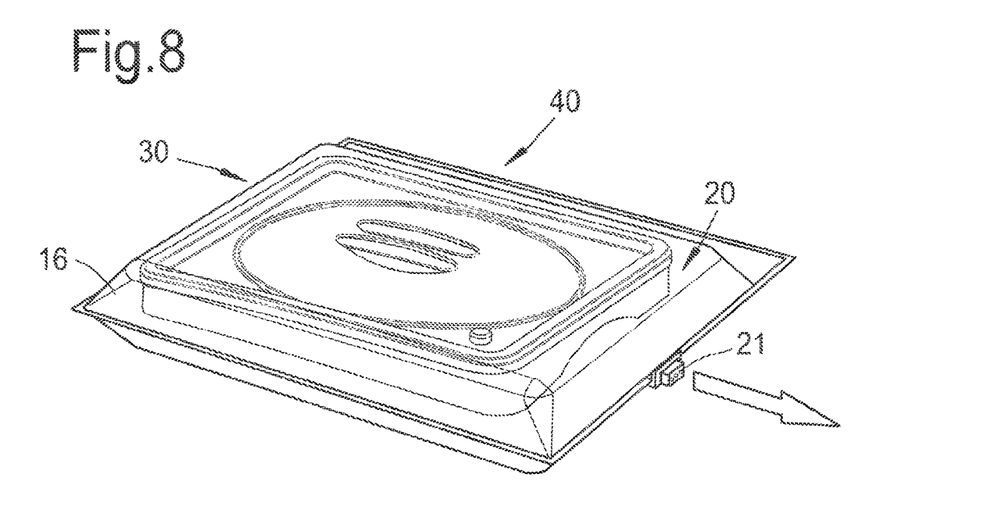
FIG. 8 shows the inner chamber of FIG. 3 and outer chamber of FIG. 4 combined to form the vacuum storage system of the present disclosure, in the process of being evacuated.

In some embodiments, the evacuation valve 21 can be a pressure valve or a degassing valve, as shown in FIG. 12A, a duckbill valve, as shown in FIG. 12B, a flap valve, as shown in FIG. 12C, a valve comprising a single slit diaphragm, as shown in FIG. 12D or a valve comprising a double or cross shaped slit diaphragm, as shown in FIG. 12E. The evacuation valve 21 and the one-way valve 13 are fluidly coupled but they do not directly contact each other and they are not in alignment with each other, as shown in FIGS. 8 and 13.

In some embodiments, the evacuation valve 21 can be made from a material, such as, for example, polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), rubber, plastic (e.g., polycarbonates), ABS, MABS, silicone, or the like or combinations thereof.

Figure 5:
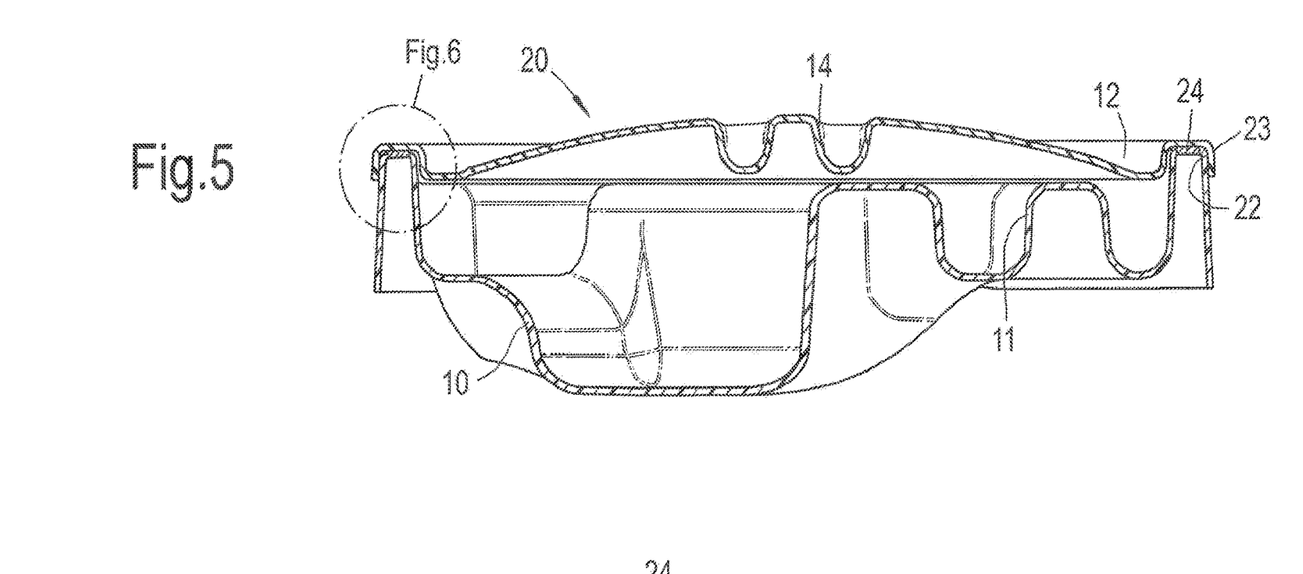
FIG. 5 shows a cross-sectional view of the inner chamber of FIG. 3.
Figure 6:
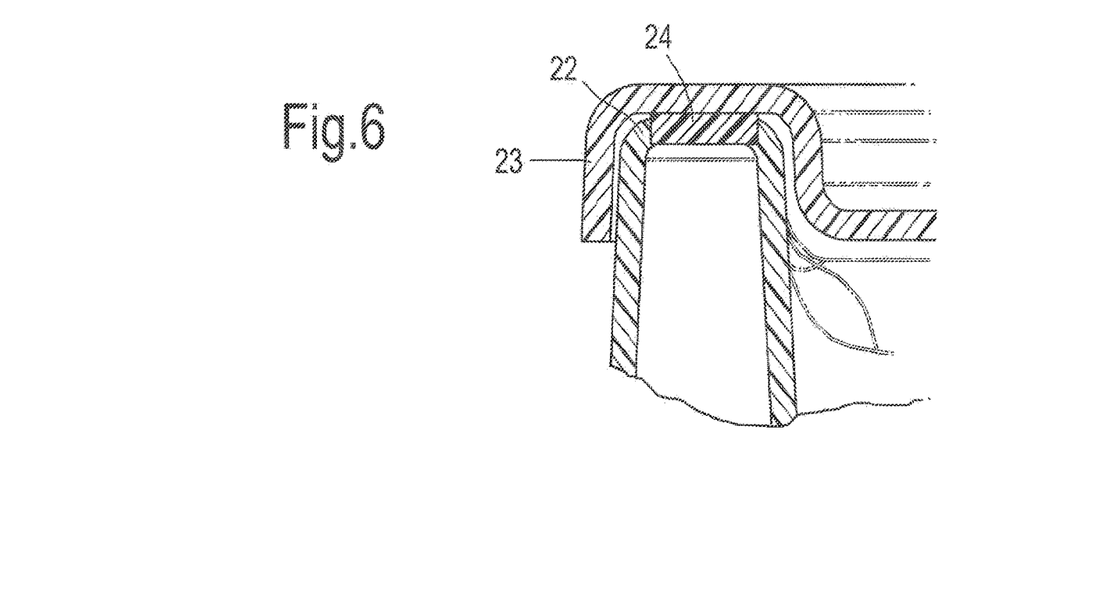
FIG. 6 shows an enlarged detail of the inner chamber of FIG. 5.

Referring now to FIGS. 5 and 6, there are shown cross-sectional views of the inner chamber 20, comprising the tray 10 and the lid 12. FIG. 6 shows an enlarged detail of the circled area of FIG. 5. As can be seen, the tray 10 is formed with a rim 22 defining the periphery thereof. The lid 12 is formed with a lip 23 of complementary size and shape to the tray rim 22, extending around the periphery of the lid 12, and adapted to engage with the tray rim 22. A gasket seal 24 is housed within the lid lip 23, and also extends around the periphery of the lid 12. When the lid 12 is engaged with the tray 10, as shown in FIGS. 5 and 6, the gasket seal 24 is compressed, to seal the inner chamber 20.

Figure 7:
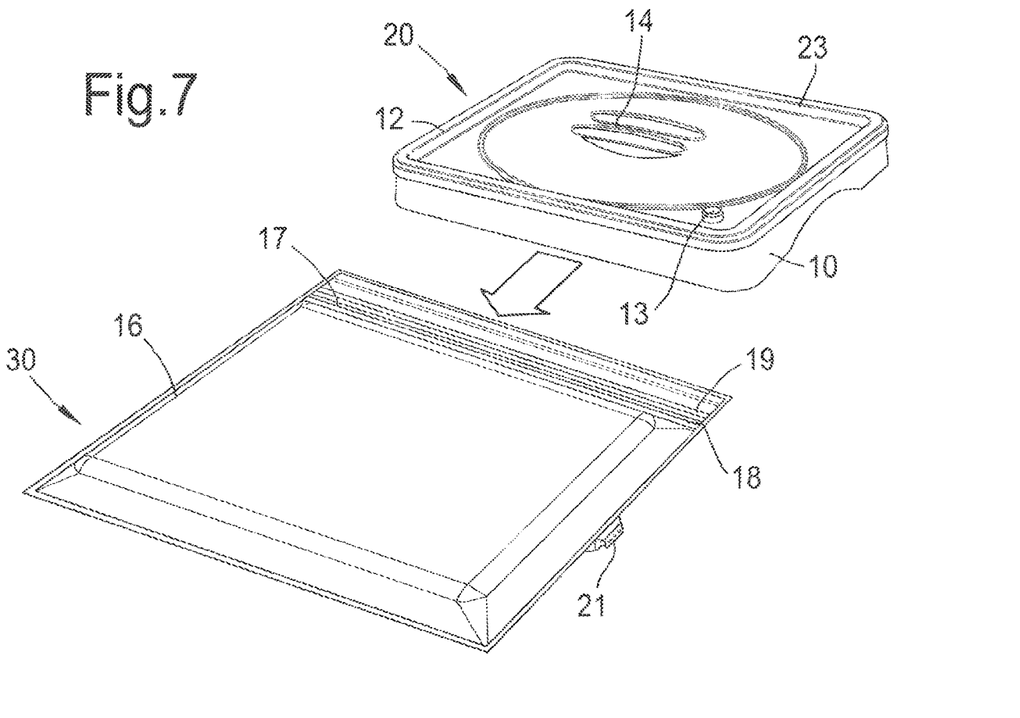
FIG. 7 shows the inner chamber of FIG. 3 being inserted into the outer chamber of FIG. 4, to form the vacuum storage system of the present disclosure.

Referring now to FIG. 7, this shows the inner chamber 20, comprising the tray 10 and lid 12 engaged therewith, being inserted into the flexible pouch 16 constituting the outer chamber 30. This is done via the opening 17 in the pouch 16, which is subsequently sealed with the double zip seal 18 and adhesive seal 19.

Referring now to FIG. 8, this shows the inner chamber 20 now fully housed within the outer chamber 30, to form a vacuum storage system, generally indicated 40, according to an embodiment of the first aspect of the present disclosure. The system 40 is now ready for evacuation, by connecting the evacuation valve 21 to suction device 48.

As shown in FIG. 13, tray 10 including inner chamber 20 and lid 12 are fully housed/disposed within the outer chamber 30 of the pouch 16 such that the inner chamber 20 does substantially contact the environment outside of the outer chamber 30. The reprocessed endoscope 15 is stored within the inner chamber 20 of the tray 10, as shown in FIG. 9. The double zip seal 18 and the adhesive seal 19 are then used to seal the outer chamber 30. In this configuration, air is in the outer chamber 30 as well as in the inner chamber 20, and the pouch 16 is disposed loosely around the tray 10 and lid 12.

When suction device 48 is attached to evacuation valve 21 of the pouch 16 via vacuum hose 50, suction from the suction device 48 will remove air from the inner chamber 20 first as among other things, the volume of this chamber is smaller than the volume of the outer chamber 30, this will urge the lid 12 onto the tray 10 to form a sealable inner chamber 20. In addition, in various embodiments, the pouch 16 will collapse entirely on the tray 10 and further urge the lid 12 onto the tray 10. The suction will be discontinued and the one-way valve 13 and the evacuation valve 21 will be both closed and the pouch is wrapped tightly on and around the tray in a shrink-wrap style maintaining the high-level disinfection status of the seal and the package integrity of the reprocessed endoscope 15 stored within the inner chamber 20 of the tray 10.

In some embodiments, the pouch 16 will leave a small gap between the pouch 16 and the one-way valve 13 of the lid 12 so that the valve 13 still functions. In some embodiments, the seal thickness is smaller for the one-way valve 13 of the lid 12 compared to the thicker one-way seal of the evacuation valve 21. The smaller thickness of the seal 46 of the one-way valve 13 allows the one-way valve 13 to open quickly so that the inner chamber 20 is evacuated before the outer chamber 30. In some embodiments, the thickness of the seal 46 of the one-way valve 13 is from about 0.5 mm to about 6 mm and the thickness of the seal 56 of the evacuation valve 21 is from about 1 mm to about 8 mm.

The air flowing through outer chamber 30 is also evacuated out of outer chamber 30 by the suction device 48, thereby evacuating outer chamber 30. One-way valve 13 disposed on the lid 12 opens upon application of suction (which results in a pressure change between the outer chamber 30 and the inner chamber 20) from the suction device 48 such that air within inner chamber 20 of the tray 10 is evacuated first from the inner chamber 20. In some embodiments, the air in outer chamber 30 will evacuate second and the pouch 16 will collapse on the tray 10 also causing the lid 12 to seal the tray 10. After application of suction is discontinued, the one-way valve 13 closes due to a change in pressure, as there is now nearly no pressure difference between the evacuated inner chamber 20 and the evacuated outer chamber 30. At this point, the pouch 16 has collapsed entirely around the tray 10. In this configuration, the reprocessed endoscope 15 maintains disinfection and is not subjected to external environmental factors.

The one-way valve 13 and evacuation valve 21 provide two independent evacuated environments. Thus, there is a first environment inside of the outer chamber 30 but outside of the inner chamber 20. When the one-way valve 13 on lid 12 is closed, the inner chamber 20 is isolated from the first environment. Thus, there is a second environment inside of the inner chamber 20. If the vacuum in the flexible outer chamber 30 subsequently fails, this can be easily visually identified by the partial re-inflation of the flexible pouch 16. This feature, among other things, provides a fail-safe measure to maintain high level disinfection status (HLDS). Further, evacuation of the outer chamber 30 of the flexible pouch 16 causes the pouch 16 to urge the lid 12 onto the tray 10. This allows an additional fail-safe protection measure for keeping the reprocessed endoscope 15 in high level disinfection.

In some embodiments, a pressure differential will exist between the inner chamber 20 of the tray 10 and the pressure within the outer chamber 30 of the pouch 16 when the tray 10 is housed/disposed within the pouch 16 and suction or no suction is applied to the system. In some embodiments, the pressure differential can be from about 0.5 to about 10 pounds per square inch (PSI). In some embodiments, the pressure differential can be from about 0.5, 0.6, 0.7, 0.8, 0.9, 1, 2, 3, 4, 5, 6, 7, 8, 9 to about 10 pounds per square inch (PSI).

In some embodiments, the vacuum storage system does not include gas scavengers or desiccants. In some embodiments, gas scavengers include, but are not limited to oxygen scavengers such as finely-divided iron powders, such as those sold under the trademark ATCO.

In some embodiments, a method, according to an embodiment of the second aspect of the present disclosure, of storing a flexible medical endoscope 15 in the vacuum storage system 40, according to an embodiment of the first aspect of the present disclosure, will now be described with reference to FIGS. 1 to 8.

Endoscope 15 is placed in the tray 10, as shown in FIGS. 1 and 9. Endoscope 15 is arranged such that its coils are embraced and protected by the upstanding elements 11. The lid 12, as shown in FIG. 2, is then placed on top of the tray 10, with the lid lip 23 engaging with the tray rim 22, as shown in FIGS. 3, 5 and 6. The inner chamber 20 of the vacuum storage system 40 is thus formed, with gasket seal 24 disposed between the tray rim 22 and the lid lip 23.

The inner chamber 20 is then inserted into the pouch 16, constituting the outer chamber of the vacuum storage system 40, as shown in FIG. 4. As illustrated in FIG. 7, the inner chamber 20 is inserted through the opening 17. The double zip seal 18 and the adhesive seal 19, are then used to seal the outer chamber 30. The vacuum storage system 40 is thus now fully formed, as shown in FIG. 8.

The evacuation valve 21 is then connected to suction device 48 for evacuation of the outer chamber 30. Activation of the suction device evacuates the outer chamber 30, and the reduction in pressure in the outer chamber 30 causes the one-way valve 13 in the lid 12 to open, thus also resulting in evacuation of the inner chamber 20. The reduction in pressure also causes the pouch 16 to collapse around the inner chamber 20, thus urging the lid 12 onto the tray 10, and compressing the gasket seal 24, so as to seal the inner chamber 20.

The suction device is then deactivated and disconnected, and the evacuation valve 21 closed. Deactivation of the suction device also causes the one-way valve 13 to close, thus fully sealing the inner chamber 20. The vacuum storage system 40 of the present disclosure thus incorporates a fail-safe mechanism in that, even if the vacuum in the outer chamber 30 is compromised due to leaking of the seals 18, 19 or the valve 21, the inner chamber 20 will remain in an evacuated state due to the one-way valve 13 remaining in a closed position, and the compressed gasket seal 24. The endoscope within the inner chamber 20 can thus be stored in a viable HLDS condition for considerably longer than with conventional storage systems.

What is claimed is:

1. A vacuum storage system for storing an article, comprising: a sealable outer chamber, having an evacuation valve for connection to a suction device for evacuation of said outer chamber; and a sealable inner chamber adapted to receive said article, and having a one-way valve in communication with the outer chamber, said one-way valve being adapted to open upon the application of suction to the outer chamber, thereby to enable evacuation of said inner chamber, but to close upon discontinuation of said suction, wherein the inner chamber comprises a tray and a lid, and the one-way valve is disposed on the lid such that the outer chamber and the inner chamber are configured to provide two independent evacuated environments, wherein the lid has a lip, and a gasket seal is housed within the lip and extends around the periphery of the lid such that the gasket seal is adapted to be compressed upon evacuation of the system and the outer chamber, when evacuated, is collapsed entirely on the tray and urges the lid onto the tray.

2. A vacuum storage system as claimed in claim 1, wherein the tray and lid are generally rigid.

3. A vacuum storage system as claimed in claim 1, wherein an interior of the tray is shaped so as to securely house the article to be stored.

4. A vacuum storage system as claimed in claim 1, wherein the outer chamber comprises a flexible pouch.

5. A vacuum storage system as claimed in claim 4, wherein the flexible pouch has an opening to enable insertion of the inner chamber, said opening being provided with a zip seal and/or an adhesive seal.

6. A vacuum storage system as claimed in claim 1, further comprising an oxygen scavenging agent, provided within the inner chamber.

7. A method of storing an article utilising a vacuum storage system as claimed in claim 1, comprising the steps of: inserting the article to be stored into the inner chamber of said vacuum storage system; sealing the inner chamber; inserting the inner chamber into the outer chamber of said vacuum storage system; sealing the outer chamber; connecting the evacuation valve of the outer chamber to a suction device; activating the suction device so as to evacuate the outer chamber, and thereby to cause the one-way valve of the inner chamber to open, so as also to evacuate the inner chamber; deactivating the suction device so as to close the one-way valve, thus isolating the article in the evacuated inner chamber; and closing the evacuation valve, thus isolating the inner chamber in the evacuated outer chamber.

8. A method as claimed in claim 7, wherein the article to be stored is an article of medical equipment.

9. A method as claimed in claim 7, wherein the article to be stored is a flexible medical endoscope.

10. A method as claimed in claim 7, further comprising an additional step of providing an oxygen scavenging agent within the inner chamber.

* * * * *